United States Patent [19]

Scremin et al.

[11] 3,984,484

[45] Oct. 5, 1976

[54] DISTILLATION IN RASCHIG-PHENOL PROCESS

[75] Inventors: Eric Hermann Scremin, Niagara Falls, N.Y.; Jay Peter Eggert, Bellefonte, Ky.

[73] Assignee: Hooker Chemicals & Plastics Corporation, Niagara Falls, N.Y.

[22] Filed: June 28, 1971

[21] Appl. No.: 157,599

Related U.S. Application Data

[63] Continuation of Ser. No. 704,300, Feb. 9, 1968, abandoned.

[52] U.S. Cl. ............................................. 260/629
[51] Int. Cl.² .................................... C07C 37/02
[58] Field of Search......... 260/629, 650, 623, 627 R

[56] References Cited
UNITED STATES PATENTS

| | | | |
|---|---|---|---|
| 2,988,573 | 6/1961 | Siebentrih et al. | 260/629 |
| 3,213,146 | 10/1965 | Prahl et al. | 260/629 |
| 3,221,063 | 11/1965 | Prahl et al. | 260/629 |
| 3,234,291 | 2/1966 | Kelly | 260/629 |

Primary Examiner—James O. Thomas, Jr.
Assistant Examiner—W. B. Lone
Attorney, Agent, or Firm—Peter F. Casella; Howard M. Ellis

[57] ABSTRACT

In a continuous process for the production of phenol by the oxychlorination of benzene to form chlorination product comprising monochlorobenzene, dichlorobenzene and benzene in a first stage, and the hydrolysis in a second stage with steam of material comprising monochlorobenzene to form hydrolysis product comprising phenol, monochlorobenzene and HCl, the method of separating and recovering phenol therefrom which comprises (1) mixing hydrolysis product comprising phenol and monochlorobenzene with chlorination product comprising monochlorobenzene, dichlorobenzene and benzene, to form liquid organic mixed product, and (2) passing said liquid organic mixed product through a distillation train, in which a benzene fraction, a fraction comprising monochlorobenzene and dichlorobenzene, and a fraction consisting essentially of phenol, ar separated therefrom. The fraction comprising monochlorobenzene and dichlorobenzene is fed to the hydrolysis stage condensation column as quenching material.

7 Claims, 1 Drawing Figure

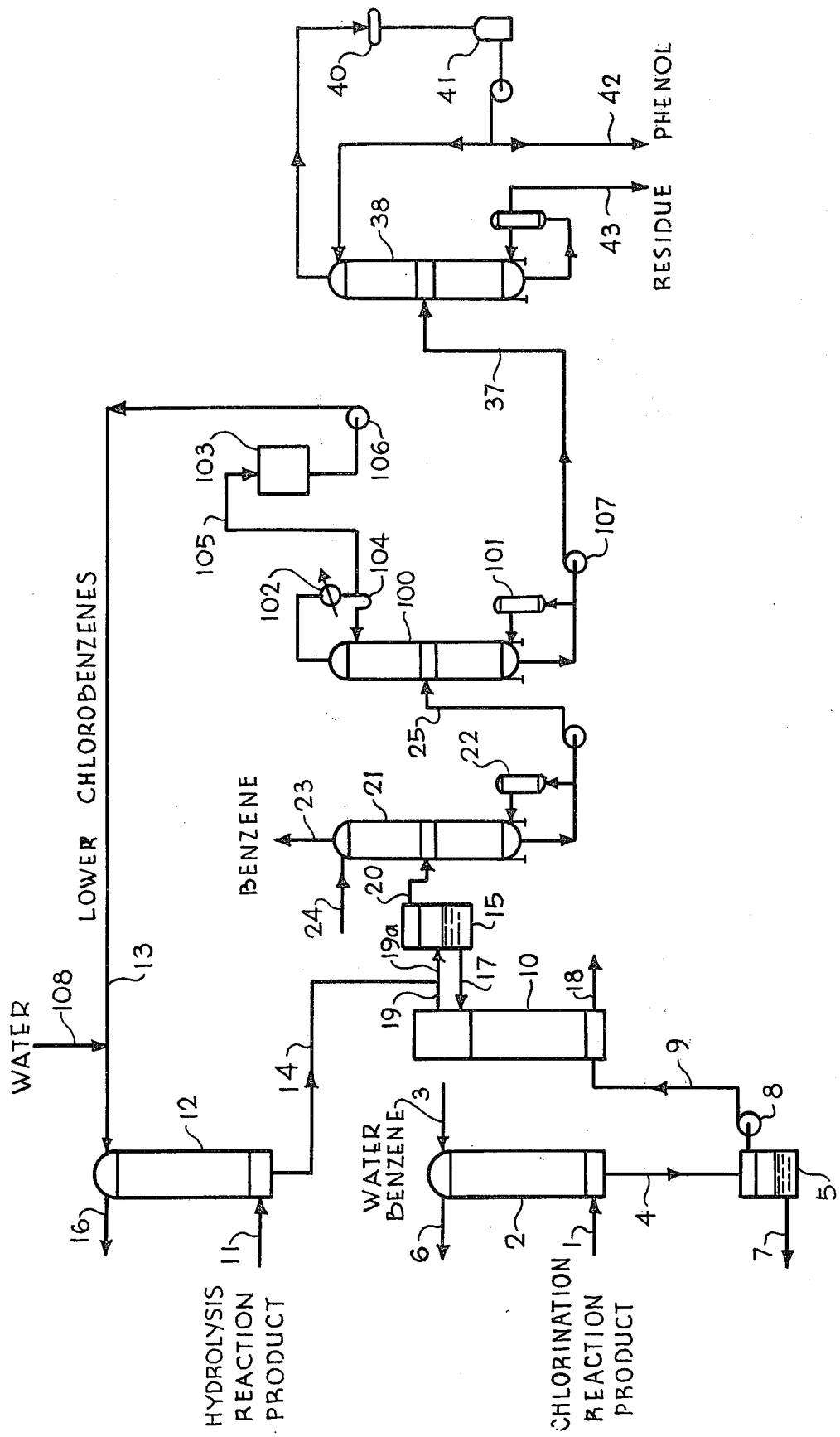

DISTILLATION IN RASCHIG-PHENOL PROCESS

This application is a continuation of Ser. No. 704,300 filed Feb. 9, 1968, now abandoned.

This invention refers to the production of phenol by the combination of the oxychlorination of benzene and the hydrolysis of monochlorobenzene, and more particularly to an integrated distillation method in the so-called Raschig-phenol process.

In the first or oxychlorination stage, the chlorination reaction produces, in addition to monochlorobenzene, certain by-products, including dichlorobenzenes, trichlorobenzenes, tetrachlorobenzenes, pentachlorobenzenes, hexachlorobenzenes and other products formed by the interaction of benzene, hydrochloric acid, and the oxygen-containing gas. The chlorination reaction product is condensed in a quench or distillation column to form liquid chlorination product. The quenching means may be water, or a mixture of benzene and water.

In the second or hydrolysis stage the hydrolysis reaction produces, in addition to the main products of phenol and hydrogen chloride, lesser amounts of benzene, chlorophenols, and high boiling tarry by-products. The hydrolysis product is condensed in a quench or distillation column to form liquid hydrolysis product. The quenching means usually comprise monochlorobenzene and water.

The liquid hydrolysis product is then mixed with the liquid chlorination product to form a two-phase mixed product having an organic-phase and a water-phase. The organic-phase is separated from the aqueous-phase to form a liquid organic mixed product, from which the phenol contained therein is separated therefrom in a distillation train in accordance with U.S. Pat. No. 3,221,063.

The resultant hydrolysis reaction liquid product has two phases. Since both of them contain phenol, both phases are preferably used in the mixing step.

The resultant chlorination reaction liquid product also has two phases and it is preferred to first separate the water-phase from the organic-phase and use the organic-phase, preferably after using it for the extraction of the phenol from the aqueous-phase of the mixed product, to mix the hydrolysis stage condensation product. The water-phase may be used elsewhere in the process, such as with monochlorobenzene to condense the hydrolysis reaction product.

The mixing of the liquid product of the two reaction stages according to U.S. Pat. No. 3,221,063, to form the organic mixed product, can be carried out by several methods, in any sequence, and partially or totally. A preferred method is to use the condensed organic products of the chlorination stage for the purpose of extracting the phenol dissolved in the acid of the aqueous-phase produced in the hydrolysis stage, and effecting the mixing operation. For example, the organic-phase separated from the liquid chlorination product can be introduced near the bottom of a liquid-liquid extraction zone into which has been introduced near the top of the phenol-containing aqueous-phase separated from the resultant mixed materials, withdrawing a phenol-enriched organic-phase from the top of said liquid-liquid extraction zone and co-mingling it with the liquid hydrolysis product. This in turn is separated into an upper organic-phase of mixed organic product to be distilled, and the lower phenol-containing aqueous-phase to be extracted. Another method is to extract phenol from the aqueous-phase of the hydrolysis product with the organic-phase of the chlorination product, and then co-mingle the resultant phenol-containing organic chlorination product with the organic-phase of the hydrolysis product to form a two-phase mixed product, which in turn is separated into the organic mixed product to be distilled.

In the modified Raschig-phenol process described in U.S. Pat. No. 3,221,063, the organic condensates from the first (benzene oxychlorination) and second (hydrolysis) stages are mixed or co-mingled, and the mixed organic product is passed through a distillation train in which the benzene is removed overhead in a first column, the monochlorobenzene is removed overhead in a second column, and an azeotropic-type mixture comprising dichlorobenzene, trichlorobenzene, chlorophenol, and some phenol is removed overhead in a third column. The bottoms from this third column, containing phenol and small quantities of dichlorobenzene, trichlorobenzene, chlorinated phenols and other high boiling compounds, are then sent to a fourth or phenol purification column. In this fourth column phenol is distilled overhead as U S P (plastics grade) phenol. The bottoms from this fourth column represent the residue from the process.

The benzene vapor from the first column in the distillation train is sent back to the first stage of the Raschig-phenol process for reuse.

The distillate from the second column, containing monochlorobenzene, is generally used in the second stage of the Raschig-phenol process by being fed as reflux to the quench column for the second stage.

The distillate from the third column is usable as feed to the second stage of the Raschig-phenol process, as described in U.S. Pat. No. 3,213,146, to be converted to phenol. However, the distillate does require vaporization prior to injection into the feed stream to the hydrolysis stage.

Under the system of the prior art, both the second and third distillation columns were needed because the monochlorobenzene and the dichlorobenzene fractions were deliberately routed to different points in the process. That is, the monochlorobenzene fraction (from the second column) was fed to the top of the second (or hydrolysis) stage quench column, and the dichlorobenzene (from the third column) was fed to the hydrolysis stage vapor recycle loop. For if the dichlorobenzene fraction from the third column were fed to the top of the second stage distillation and condensation column, it was considered the dichlorobenzene would tend to build up in concentration in the bottoms, and thus increase in concentration in the mixed organic product being fed into the distillation train. Moreover, the third column was operated at conditions different from the second column, (e.g., under vacuum), in order to effect a separation of phenol and dichlorobenzene in which the ratio of dichlorobenzene to phenol was an economic maximum. Maintaining the third column under this high vacuum also necessitated larger more expensive equipment and auxiliary systems such as vacuum pumps, than on the second column, which increased the investment and operating cost of the overall process. In addition, the distillate from the third column had to be re-evaporated for routing through the catalyst chamber of the second or hydrolysis stage. This extra evaporator also increased the investment and operating expense. Moreover, even when operating the third column under relatively high vacuum and appreciable quantity of phenol is still recycled in the dichlorobenzene fraction back to the second or hydrolysis stage of the Raschig-phenol process.

Another method has now been found to recover the dichlorobenzene being distilled from the co-mingled or mixed organic product and to feed it to the second stage of the Raschig-phenol process without the use of the third or dichlorobenzene distillation column and the auxiliary evaporator, which comprises passing the liquid organic mixed product through a new distillation train, distilling overhead a benzene fraction, distilling overhead a fraction comprising monochlorobenzene, dichlorobenzene, trichlorobenzene, and chlorophenol, feeding this fraction to the top of the hydrolysis stage quench column, and distilling overhead a fraction consisting essentially of phenol.

Thus, the second and third distillation columns in the process of U.S. Pat. No. 3,221,063 and the auxiliary evaporation equipment are eliminated by this process, and replaced with just one distillation column. This is surprising because it was thought that if the dichlorobenzene fraction from the third column were fed to the top of the hydrolysis quench column, the dichlorobenzene would tend to build up and concentrate in the bottoms of the quench column; and therefore, the dichlorobenzene would tend to continually increase in concentration in the mixed organic product being fed into the first column of the distillation train. It has been unexpectedly found however, that the composition of the mixture of materials in the quench column is such that most of the dichlorobenzene fed is evaporated overhead rather than being condensed. The dichlorobenzene is thus channelled into the vapor phase recycle loop and from there into the hydrolysis zone for conversion to phenol.

In addition, it has been unexpectedly found that by evaporating overhead in one column both the monochlorobenzene fraction and the dichlorobenzene fraction of the process of U.S. Pat. No. 3,221,063, an effective ratio of phenol to dichlorobenzene is achieved which is actually lower than the ratio had been in the third column. That is, in the former column the mole ratio of phenol to dichlorobenzene ranged from a low of about 1:4 to above 1:2; whereas, in the new distillation of this invention the mole ratio of phenol to dichlorobenzene has been unexpectedly found to be from as low as 1:99 to about 1:20. It is to be understood that with both monochlorobenzene and dichlorobenzene present in the new overheads, the total amount of distillate in the overheads is greater than the third column of the former process, but the net overall amount phenol being retained to the process is much lower.

This new column is operated at substantially atmospheric pressure although pressures somewhat above or below atmospheric may be used. That is, the vacuum required in the third column of the former process, is no longer needed. The temperature at the bottom of the new column is approximately the boiling point of phenol at the prevailing pressure and purity in the column. This may be between about 180° and 190° centigrade.

By operation in accordance with this invention therefore the following savings are realized: The third or dichlorobenzene column of U.S. Pat. No. 3,221,063, and its auxiliary equipment are eliminated. The auxiliary evaporator for re-evaporating the dichlorobenzene fraction for feeding to the second stage, is also eliminated. Also, reducing the amount of phenol being returned to the second stage of the process contributes to increase the overall production.

An auxiliary saving and advantage to this process can be seen from the fact that in the old process a multistage steam jet ejector vacuum system was used to maintain the vacuum in the third column. This presented a problem of potential water pollution. However, with the process of this invention, wherein the third column has been eliminated, this investment and operating expense, and the potential pollution problem have also been eliminated. If on the other hand a mechanical vacuum system had been used to maintain the vacuum in the third column, there would be a maintenance and mechanical problem with the vacuum pump tending to break down at frequent intervals; thus this is eliminated.

Referring to the FIGURE, the reacted product mixture from the chlorination (stage 1) zone, comprising unreacted benzene, lower and higher chlorobenzenes, steam and some hydrogen chloride (HCl), enters in vapor form through duct 1 a chlorination distillation and condensation column 2, where by means of liquid benzene and water fed into column 2 through pipe line 3, the chlorinated benzene and hydrochloric acid, together with unreacted benzene are scrubbed or condensed out as a two-phase liquid chlorination product, and leaves column 2 through pipe 4 into a gravity separator 5 where the liquid separates into a lower water-phase chlorination product and an upper organic-phase chlorination product comprising monochlorobenzene lower and higher polychlorobenzenes, and benzene. The water-phase is withdrawn from the gravity separator 5 through pipe 7 and returned to the Raschig-phenol process. The organic-phase chlorination product is withdrawn from gravity separator 5 and passes through pump 8 and pipe 9 into the bottom of liquid-liquid extraction column 10. The vaporous materials at the top of column 2, comprising benzene, water and inerts, are withdrawn through line 6 and further processed.

The reacted product mixture from the hydrolysis (stage 2) zone, comprising phenol, steam, HCl, unconverted monochlorobenzene, and minor amounts of other products such as chlorophenol and unconverted lower polychlorobenzene, enters in vapor form through duct 11, a distillation and condensation column 12, where, by means of water and lower chlorobenzenes, comprising mainly monochlorobenzene but also containing dichlorobenzenes, trichlorobenzenes and traces of chlorophenol, entering column 12 near the top through line 13, the liquid hydrolysis product comprising phenol, HCl and water, is scrubbed or condensed out and leaves column 12 through line 14. Unreacted lower chlorobenzenes and water leave column 12 in vapor form through duct 16, to comprise the vapor recycle loop for stage 2.

In the FIGURE the liquid hydrolysis product, withdrawn from column 12 through line 14, is then co-mingled, merged, joined, or mixed with the phenol-containing organic-phase of the liquid chlorination product at the top of the liquid-liquid extraction column 10 by injecting it directly into the phenol-enriched organic material emerging from the top of column 10 through line 19. The resultant two-phase mixed product stream is then passed through line 19a into gravity separator 15, and separated into a lower phenol-containing mixed product aqueous-phase and an upper organic mixed product. The aqueous-phase, comprising phenol dissolved in about 15 to 20 percent hydrochloric acid, is withdrawn through line 17 and passed into the top portion of the liquid-liquid extraction column 10 where its phenol content is extracted as the aqueous-phase passes down through the column in counter-current flow to the upward rising organic-phase benzene-monochlorobenzene material entering the bottom portion of column 10 through line 9. The extracted aqueous-phase leaves column 10 through line 18 for re-use in the chlorination stage of the process. Although this is the preferred method of mixing the liquid hydrolysis product with the liquid chlorination product, other methods of mixing, merging or co-mingling the two products can be used to obtain the desired organic mixed product to be passed through the subsequent distillation train.

The organic layer leaving the top of the gravity separator 15 through line 20 comprises all of the organic constituents produced in the process, as well as traces of water and hydrogen chloride. The hydrogen chloride content of the organic mixed product is normally quite small, but nevertheless it is ordinarily necessary to remove it in order to prevent corrosion in the distillation train. Removal of this hydrogen chloride can be effected, for instance, by neutralization with sodium hydroxide, sodium carbonate, lime, or other alkaline substances, or by azeotropic distillation in a column protected from corrosion by HCl, or by any other means known to the art.

The organic mixed product in line 20 therefore constitutes the starting mixture of the liquid products of the two stages to be distilled in accordance with the teachings of this invention. This starting mixture in line 20 passes into fractionation column 21 equipped with reboiler 22, in which a product consisting essentially of benzene is driven off, exiting from column 21 in vapor form through duct 23 for re-use in the process, while the higher boiling substances are kept back by a reflux of liquid benzene entering through line 24.

The column 21 bottoms, substantially free of benzene, enter through line 25, a novel distillation column 100 equipped with reboiler 101, condenser 102, and receiver 103. This column drives over substantially all of the lower chlorobenzenes, comprising mainly monochlorobenzene, as well as the lower polychlorobenzenes, plus trace quantities of chlorophenols, and a small quantity of phenol. A portion of the condensed distillate leaving condenser 102 is returned as reflux for column 100, through line 104. The remainder of the distillate passes through line 105 to the receiver 103. From the receiver, the distillate lower chlorobenzenes are preferably passed via pump 106 and line 13 to where water is added through line 108 and the material used as quenching means for column 12.

The column 100 bottoms of this novel distillation, comprising phenol and higher boiling substances, passes via pump 107 and line 37 into a third distillation column 38, equipped with reboiler 39, condenser 40, and receiver 41. This column drives over substantially pure phenol, which is removed through line 42 for commercial use. The residue from column 38 containing the higher boiling substances, leaves the system through line 43.

It is obvious to those of ordinary skill in this art that the purpose of recovering commercial products out of the mixture of the products of the chlorination and hydrolysis reaction of the Raschig-phenol process can be achieved by numerous other methods of mixing and/or distilling, without departing from the spirit of this invention, and the invention herein is not to be limited hereto except as defined in the appended claims.

We claim:

1. In a continuous process for the production of phenol by the oxychlorination of benzene to form chlorination product comprising monochlorobenzene, dichlorobenzene and benzene in a first stage, the hydrolysis in a second stage with steam of material comprising monochlorobenzene to form hydrolysis product comprising phenol, monochlorobenzene and HCl, and the recovery of phenol; the improvement in the recovery of phenol which comprises (1) mixing hydrolysis product comprising phenol and monochlorobenzene with chlorination product comprising monochlorobenzene, dichlorobenzene and benzene to form liquid organic mixed product, and (2) passing said liquid organic mixed product through a distillation train in which a first fraction comprising benzene, a second fraction comprising monochlorobenzene and dichlorobenzene, and a third fraction consisting essentially of phenol, are separated therefrom, wherein said second fraction is separated from the fraction comprising phenol at approximately the boiling point of phenol at the prevailing pressure and purity, and (3) passing said second fraction to the hydrolysis product condensation zone.

2. In a continuous process for the production of phenol by the oxychlorination of benzene to form chlorination product comprising monochlorobenzene, higher and lower polychlorobenzene and benzene in a first stage, the hydrolysis in a second stage with steam of material comprising monochlorobenzene to form hydrolysis product comprising phenol, monochlorobenzene, steam and HCl, and recovery of phenol; the improvement in the recovery of phenol which comprises (1) introducing said hydrolysis product near the bottom of a hydrolysis product condensation zone into the top of which is being fed material comprising the second fraction from step (3) to produce hydrolysis condensation product comprising phenol, monochlorobenzene and lower polychlorobenzene, (2) mixing the hydrolysis condensation product with chlorination product comprising monochlorobenzene, lower and higher polychlorobenzene and benzene, to form a liquid organic mixed product, (3) passing said liquid organic mixed product through a distillation train in which a first fraction comprising benzene is separated therefrom in a first distillation column of said distillation train, a second fraction comprising monochlorobenzene and lower polychlorobenzene is separated therefrom in a second distillation column while maintaining a temperature at the bottom of said second distillation column which is approximately the boiling point of phenol at the prevailing pressure and purity in said column, and a third fraction consisting essentially of phenol is separated therefrom in a third distillation column, and (4) feeding said second fraction to the top of the hydrolysis product condensation zone.

3. In a continuous process for the production of phenol by the oxychlorination of benzene to form chlorination product comprising monochlorobenzene, higher and lower polychlorobenzene and benzene in a first stage, the hydrolysis in a second stage with steam of material comprising monochlorobenzene to form hydrolysis product comprising phenol, monochlorobenzene, steam and HCl, and the recovery of phenol; the improvement in the recovery of phenol which comprises (1) condensing said chlorination product to form chlorination condensation product comprising monochlorobenzene, higher and lower polychlorobenzene, benzene and water, (2) condensing said hydrolysis product with material comprising the fraction from step (6), to form hydrolysis condensation product comprising phenol, monochlorobenzene and water, (3) mixing hydrolysis condensation product and chlorination condensation product to form a two-phase liquid mixed product having an organic-phase and an aqueous phase, (4) separating the organic-phase from the aqueous-phase in said two-phase liquid mixed product, to form liquid organic mixed product, and (5) passing said liquid organic mixed product through a first distillation column in which a fraction comprising benzene is separated therefrom, (6) subsequently passing the resulting liquid organic mixed product through a second distillation column in which a fraction containing monochlorobenzene and lower polychlorobenzenes are separated therefrom while maintaining a temperature at the bottom of said column which is approximately the boiling point of phenol at the prevailing pressure and purity in the column, and (7) subsequently passing the resulting liquid organic mixed product through a third distillation column in which a fraction consisting essentially of phenol is separated therefrom.

4. In a continuous process for the production of phenol by the oxychlorination of benzene to form chlorination product comprising monochlorobenzene, higher and lower polychlorobenzene and benzene in a first stage, the hydrolysis in a second stage with steam of material comprising monochlorobenzene to form hydrolysis product comprising phenol, monochlorobenzene, steam and HCl, and the recovery of phenol; the improvement which comprises the steps of: (1) condensing said chlorination product, to form two-phase chlorination condensation product having an organic-phase and a water-phase, (2) separating the water-phase from the organic-phase of said liquid chlorination product, to form liquid organic-phase chlorination product comprising monochlorobenzene, higher and lower polychlorobenzene and benzene, (3) condensing said hydrolysis product with material from the second distillation fraction of step (7), to form hydrolysis condensation product comprising phenol, monochlorobenzene, lower polychlorobenzenes, and water, (4) co-mingling the said hydrolysis condensation product with phenol-enriched organic chlorination product of step (6), to form two-phase liquid mixed product having an organic-phase and an aqueous-phase, (5) separating the organic phase from the aqueous phase of said two-phase liquid mixed product of step (4), to form an aqueous mixed product containing phenol and liquid organic mixed product, (6) extracting the phenol from the said aqueous mixed product of step (5) with the said organic phase of the said chlorination product, to form phenol-enriched organic chlorination product, and (7) passing the liquid organic mixed product of step (5) through a distillation train in which a first fraction comprising benzene is separated therefrom in a first distillation column of said distillation train, a second fraction comprising monochlorobenzene and lower polychlorobenzene is separated therefrom in a second distillation column while maintaining a temperature at the bottom of said second distillation column which is approximately the boiling point of phenol at the prevailing pressure and purity in said second column, and a third fraction consisting essentially of phenol is separated therefrom in a third distillation column.

5. In a continuous process for the production of phenol by the oxychlorination of benzene to form chlorination product comprising monochlorobenzene, higher and lower polychlorobenzene and benzene in a first stage, and the hydrolysis in a second stage with steam of material comprising monochlorobenzene, lower polychlorobenzene and chlorophenol to form hydrolysis product comprising phenol, monochlorobenzene, lower polychlorobenzene, chlorophenol, steam and HCl, and the recovery of phenol; the improvement which comprises: (1) condensing said chlorination product, to form chlorination condensation product comprising monochlorobenzene, higher and lower polychlorobenzene, benzene and water, (2) condensing said hydrolysis product with material comprising the second distillation fraction from step (5) to form hydrolysis condensation product comprising phenol, monochlorobenzene, lower polychlorobenzene, chlorophenol and water (3) mixing said hydrolysis condensation product with said chlorination condensation product, to form a two-phase liquid mixed product having an organic-phase and an aqueous-phase, (4) separating the organic-phase from the aqueous-phase of said two-phase liquid mixed product, to form liquid organic mixed product, and (5) passing said liquid organic mixed product through a distillation train in which a first fraction comprising benzene is separated therefrom in a first distillation column of said distillation train, a second fraction comprising monochlorobenzene and lower polychlorobenzene is separated therefrom in a second distillation column while maintaining a temperature at the bottom of said second distillation column which is approximately the boiling point of phenol at the prevailing pressure and purity in said column, and a third fraction consisting essentially of phenol is separated therefrom in a third distillation column.

6. In a continuous process for the production of phenol by the oxychlorination of benzene to form chlorination product comprising monochlorobenzene, higher and lower polychlorobenzene and benzene in a first stage, and the hydrolysis in a second stage with steam of material comprising monochlorobenzene, lower polychlorobenzene and chlorophenol to form hydrolysis product comprising phenol, monochlorobenzene, lower polychlorobenzene, chlorophenol, steam and HCl, and the recovery of phenol; the improvement which comprises the steps of: (1) condensing said chlorination product with water and benzene to form a two-phase chlorination condensation product having an organic-phase and a water-phase, (2) separating the water-phase from the organic-phase of the chlorination condensation product, to form liquid organic-phase chlorination product comprising monochlorobenzene, higher and lower polychlorobenzene and benzene, (3) condensing said hydrolysis product with material comprising the second distillation fraction in step (7), to form a hydrolysis condensation product comprising phenol, monochlorobenzene, lower polychlorobenzene, chlorophenol and water, (4) co-mingling said hydrolysis condensation product with the phenol-enriched organic chlorination product of step (6), to form a two-phase liquid mixed product having an organic-phase and an aqueous-phase, (5) separating the organic-phase from the aqueous-phase of said two-phase liquid mixed product of step (4) to form an aqueous mixed product containing phenol, and a liquid organic mixed product, (6) extracting the phenol from said aqueous mixed product of step (5) with said organic-phase of said chlorination product to form a phenol-enriched organic chlorination product, and (7) passing said liquid organic mixed product of step (5) through a distillation train in which a first fraction comprising benzene is separated therefrom in a first distillation column of said distillation train, a second fraction comprising monochlorobenzene and lower polychlorobenzene is separated therefrom in a second distillation column while maintaining a temperature at the bottom of said second distillation column which is approximately the boiling point of phenol at the prevailing pressure and purity in said column, and a third fraction consisting essentially of phenol is separated therefrom in a third distillation column.

7. In a continuous process for the production of phenol by the oxychlorination of benzene to form chlorination product comprising monochlorobenzene, higher and lower polychlorobenzene and benzene in a first stage, and the hydrolysis in a second stage with steam of material comprising monochlorobenzene, lower polychlorobenzene and chlorophenol to form hydrolysis product comprising phenol, monochlorobenzene, lower polychlorobenzene, chlorophenol, steam and HCl, and the recovery of phenol; the improvement which comprises the steps of: (1) condensing said chlorination product with water and benzene to form a two-phase chlorination condensation product having an organic-phase and a water-phase, (2) separating the water-phase from the organic-phase of the chlorination condensation product, to form liquid organic-phase chlorination product comprising monochlorobenzene, higher and lower polychlorobenzene and benzene, (3) condensing said hydrolysis product with the second distillation fraction in step (8), to form a hydrolysis condensation product having an organic-phase and a water-phase, (4) separating the water-phase from the organic-phase of the hydrolysis condensation product to form liquid organic-phase hydrolysis product comprising phenol, monochlorobenzene, lower polychlorobenzene and chlorophenol, and to form liquid aqueous-phase hydrolysis product comprising water, HCl and phenol, (5) extracting the phenol from the aqueous phase of the hydrolysis product with the organic phase of the chlorination product, (6) co-mingling the resultant phenol-containing organic chlorination product with the organic phase of the hydrolysis product to form a two-phase mixed product having an organic-phase and an aqueous phase, (7) separating the organic-phase from the aqueous-phase of said two-phase liquid mixed product of step (6) to form an aqueous mixed product containing phenol, and a liquid organic mixed product, and (8) passing said liquid organic mixed product of step (7) through a distillation train in which a first fraction comprising benzene is separated therefrom in a first distillation column of said distillation train, a second fraction comprising monochlorobenzene and lower polychlorobenzene is separated therefrom in a second distillation column while maintaining a temperature at the bottom of said second distillation column which is approximately the boiling point of phenol at the prevailing pressure and purity in said column, and a third fraction consisting essentially of phenol is separated therefrom in a third distillation column.

* * * * *